(12) United States Patent
Wheatley et al.

(10) Patent No.: US 6,180,105 B1
(45) Date of Patent: Jan. 30, 2001

(54) METHOD FOR PRODUCING AN EXTRACT CONTAINING ARTEMESININ

(75) Inventors: Gary William Wheatley, Hull; Thomas Brian Chapman, Brough, both of (GB)

(73) Assignee: Essential Nutrition Ltd., Brough (GB)

( * ) Notice: Under 35 U.S.C. 154(b), the term of this patent shall be extended for 0 days.

(21) Appl. No.: 09/282,763

(22) Filed: Mar. 31, 1999

(51) Int. Cl.$^7$ .................. A61K 35/78; A61K 31/355; A01N 43/02
(52) U.S. Cl. .................. 424/195.1; 514/450; 549/348
(58) Field of Search .................. 424/195.1; 514/450; 549/348

(56) References Cited

U.S. PATENT DOCUMENTS

| | | | | |
|---|---|---|---|---|
| 3,477,856 | * | 11/1969 | Schultz | 426/424 |
| 4,554,170 | * | 11/1985 | Panzner et al. | 426/651 |
| 4,632,837 | * | 12/1986 | Schutz et al. | 426/425 |
| 4,985,265 | * | 1/1991 | Duboc et al. | 426/425 |
| 5,413,928 | * | 5/1995 | Weathers et al. | 435/123 |

FOREIGN PATENT DOCUMENTS

| | | | |
|---|---|---|---|
| 1095381 | * | 5/1993 | (CN) . |
| 2317612 | * | 4/1998 | (GB) . |

OTHER PUBLICATIONS

Kohler et al. J. Chromatogr. vol 785, pp. 353–360, 1997.*
Kohler et al. Phytochem. Anal. vol. 8, No. 5, pp. 223–227, abstract enclosed, 1997.*
Khanan et al. Khim–Farm. Zh. vol. 2, No. 2, pp. 40–44, 1968.*
Sigma Chemical Catalog, p. 135 (#A 5430), 1994.*
Quellette, R. Intro. to General, Organic, and Biological Chem., 2nd ed., p. 545, 1988.*
The Condensed Chem Dictionary, 10th ed., pp. 598 (lactone), 916 (sesquiterpene), 1000 (terpene), 1981.*
Grimmett, C. Chemistry and Industry—Food Processing. vol.. 10, pp. 359–362, 1981.*
Chemical Abstract No.335344f–Ge et al., Supercritical extraction of arteanniun from Artemisia annua., May 19, 1993.
Hubert et al., Fluid Extraction of Hops, Spices & Tobacco with Supercritical Gases, *Agnew. Chem. Int. Ed. Engl.*, vol. 17, pp. 710–715, 1978.
Moyler, Estraction of Essential Oils with Carbon Dioxide, 23$^{nd}$ Int'l Symposium on Essential Oils, Scotland Sep. 9–12, 1992.
Ronyai et al., Production of Plant Extracts by Supercritical Extraction, *Olaj, Szappan, Kozmet*, vol. 45, (Special Issue), 1996.
CN 1095381 A (GE et al.) Abstract only., 1994.
Chem Abstr. (23:335344f, 1993.

* cited by examiner

*Primary Examiner*—Christopher Tate
(74) *Attorney, Agent, or Firm*—Jenkens & Gilchrist A Professional Corporation

(57) ABSTRACT

A method of preparation of an artemisinin extract comprising the steps of extraction of Artemisia annua with liquid carbon dioxide and allowing the carbon dioxide to evaporate from the resultant mixture.

30 Claims, No Drawings

METHOD FOR PRODUCING AN EXTRACT CONTAINING ARTEMESININ

This invention relates to the production of a novel extract from *Artemisia annua* which contains high levels of the known anti-malarial active Artemisinin. The invention also relates to a method of producing such an extract.

*Artemisia annua* has been used in China for many centuries for the treatment of malaria. Research in the 1970s by Chinese scientists confirmed the efficacy of preparations of *Artemisia annua* in the treatment of malaria, including the most severe and life threatening form of the disease known as cerebral malaria, caused by infection with the Plasmodium falciparum parasite. The main chemical constituent of Artemisia responsible for this pharmacological activity was identified as the unusual bridged peroxy sesquiterpene structure originally named "Qinghaosu" but now known as artemisinin. The structure of artemisinin is given below:

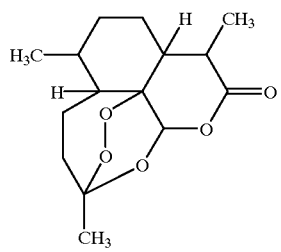

Clinical studies on artemisinin and semi-synthetic derivatives such as artemether have confirmed the efficacy of this type of compound in the treatment of malaria. Artemisinin lacks the nitrogen containing heterocyclic ring that is common to the standard anti-malarials currently used such as the aminoquinolines (quinine, chloroquine, primaquine, etc.) The problem of resistance and cross-resistance that is now beginning to seriously limit the effectiveness of these drugs is not observed for artemisinin. For example, artemisinin has been found to be effective against chloroquine resistant strains of *Plasmodium falciparum*.

Artemisinin has recently been prepared synthetically but such is the complexity of the molecule that there is no large scale economical synthetic route. This has been recognized by the vigorous research effort directed towards the synthesis of much simpler analogues of artemisinin.

Chinese researchers in their earlier studies favored extracts of Artemisia produced using non-polar organic solvents such as diethyl ether or more commonly, petroleum ether. However, these have the drawbacks that the artemisinin content was quite low and that it was difficult to completely remove trace levels of the solvent to produce a pharmaceutically acceptable product. The extraction process uses large quantities of organic solvent which must either be disposed of or recycled.

In recent years, the use of liquefied carbon dioxide extraction has been applied to the isolation of pharmaceutical actives from plant materials. This technique has been used on an industrial scale for over two decades for the extraction of flavor principles from hops and other herbs and spices. It has the advantage over extraction with conventional organic solvents that the extraction medium is readily and completely removed simply by depressurizing the extraction apparatus, thus allowing the liquid carbon dioxide to vaporize into the atmosphere. Thus, problems of waste solvent disposal and trace solvent contamination of finished product are eliminated. The selectivity of liquid carbon dioxide is generally superior to organic solvents of comparable polarity such as ethyl acetate or petroleum ether.

According to a first aspect of the present invention, a method of preparation of an artemisinin extract comprises the steps of extraction of *Artemisia annua* with solvent comprising liquid carbon dioxide and allowing the carbon dioxide to evaporate from the resultant mixture.

According to a second aspect of the present invention, there is provided an *Artemisia annua* extract containing more than 10% by weight of artemisinin, the extract not containing any residual organic solvent.

A co-solvent may be employed, for example a polar hydroxylic solvent such as $C_1$ to $C_4$ alcohol, preferably ethanol. An amount of co-solvent of 5 to 20%, preferably 10% by weight may be employed.

The resultant residual extract may have a high artemisinin content without any traces of residual non-hydroxylic solvent.

Preferred methods involve extraction at a pressure of 1500 to 4500 psi (100 to 310 bars), preferably about 1500 psi (100 bars) and at a temperature in the region of 20 to 50° C., preferably 25 to 30° C. Use of sub-critical carbon dioxide without any co-solvent is preferred.

The invention is further described by means of example but not in any limitative sense.

EXAMPLE

Roughly ground aerial parts of the herb *Artemisia annua* were packed into a pressure vessel. A volume of liquid carbon dioxide at the ratio of approximately 5 ml of liquid carbon dioxide per 1 g of herbaceous matter was allowed to pass through the raw material at a rate of approximately 0.9 ml/min. The liquid carbon dioxide was then collected, the pressure released and the carbon dioxide allowed to vent to the atmosphere. The residual extract in the collection vessel was an oil or semi-solid dependent on the exact extraction conditions.

The following range of extraction conditions were employed:

| SAMPLE | PRESSURE | TEMP | CO-SOLVENT | % YIELD (w/w) | % ARTEMESININ |
|---|---|---|---|---|---|
| Art 1 | 1500 psi | 27° C. | None | 1.1% | 14% |
| Art 2 | 1500 psi | 27° C. | 10% Ethanol | 3.2% | 3.3% |
| Art 3 | 4500 psi | 50° C. | None | 0.2% | 2.0% |
| Art 4 | 4500 psi | 50° C. | 10% Ethanol | 3.7% | 1.0% |

Extraction conditions of 1500 psi and 27° C. are equivalent to the use of subcritical liquid carbon dioxide and 4500 psi at 50° C. is equivalent to the use of supercritical carbon dioxide.

An estimate of the artemisinin content was made by semi-quantitative TLC. The use of subcritical carbon dioxide with no added organic co-solvent yielded optimum results with an approximate artemisinin content of >10% by weight being obtained for extract Art 1. All other extraction conditions yielded much lower artemisinin contents of approximately 3 % or less.

By way of comparison, a standard petroleum ether extract of Artemisia was prepared and the artemisinin content found to be 5.2% by the semi-quantitative TLC method for an overall yield of extract of 2.9%.

The artemisinin content of the raw material used was estimated by TLC to be 0.15% w/w which is in agreement with the previously published range of 0.01 to 0.6% w/w for *Artemisia annua* samples.

What is claimed is:

1. A method of preparation of an artemisinin extract comprising the steps of extrtacting ground aerial parts of *Artemisia annua* with a solvent comprising subcritical liquid carbon dioxide and allowing the carbon dioxide to evaporate from the reultant mixture to directly isolate an extract of at least 10% by weight artemisinin that does not contain residual solvent.

2. The method of claim 1, wherein the solvent comprises a mixture of liquid carbon dioxide and a polar hydroxylic solvent.

3. The method of claim 2, wherein the hydroxylic solvent is a $C_{1-4}$ alcohol.

4. The method of claim 3, wherein the hydroxylic solvent is ethanol.

5. The method of claim 2, wherein the amount of hydroxylic solvent is 5 to 20% by weight.

6. The method of claim 3, wherein the amount of hydroxylic solvent is 5 to 20% by weight.

7. The method of claim 4, wherein the amount of hydroxylic solvent is 5 to 20% by weight.

8. The method of claim 2, wherein the amount of hydroxylic solvent is 10% by weight.

9. The method of claim 3, wherein the amount of hydroxylic solvent is 10% by weight.

10. The method of claim 4, wherein the amount of hydroxylic solvent is 10% by weight.

11. The method of claim 1, wherein the extraction is carried out at a pressure of 1500 psi.

12. The method of claim 2, wherein the extraction is carried out at a pressure of 1500 psi.

13. The method of claim 3, wherein the extraction is carried out at a pressure of 1500 psi.

14. The method of claim 4, wherein the extraction is carried out at a pressure of 1500 psi.

15. The method of claim 5, wherein the extraction is carried out at a pressure of 1500 psi.

16. The method of claim 6, wherein the extraction is carried out at a pressure of 1500 psi.

17. The method of claim 7, wherein the extraction is carried out at a pressure of 1500 psi.

18. The method of claim 8, wherein the extraction is carried out at a pressure of 1500 psi.

19. The method of claim 9, wherein the extraction is carried out at a pressure of 1500 psi.

20. The method of claim 10, wherein the extraction is carried out at a pressure of 1500 psi.

21. The method of claim 11, wherein the extraction is carried out at a temperature of 25 to 30° C.

22. The method of claim 12, wherein the extraction is carried out at a temperature of 25 to 30° C.

23. The method of claim 13, wherein the extraction is carried out at a temperature of 25 to 30° C.

24. The method of claim 14, wherein the extraction is carried out at a temperature of 25 to 30° C.

25. The method of claim 15, wherein the extraction is carried out at a temperature of 25 to 30° C.

26. The method of claim 16, wherein the extraction is carried out at a temperature of 25 to 30° C.

27. The method of claim 17, wherein the extraction is carried out at a temperature of 25 to 30° C.

28. The method of claim 18, wherein the extraction is carried out at a temperature of 25 to 30° C.

29. The method of claim 19, wherein the extraction is carried out at a temperature of 25 to 30° C.

30. The method of claim 20, wherein the extraction is carried out at a temperature of 25 to 30° C.

\* \* \* \* \*

UNITED STATES PATENT AND TRADEMARK OFFICE
CERTIFICATE OF CORRECTION

PATENT NO. : 6,180,105 B1
DATED : January 30, 2001
INVENTOR(S) : Wheatley et al.

Page 1 of 1

It is certified that error appears in the above-identified patent and that said Letters Patent is hereby corrected as shown below:

Title page,
Item [54], please delete "Artemesinin" and insert -- Artemisinin --.

Item [56] Other Publications,
Please delete "CN 1095381 A (Ge et al.) Abstract only, 1994.
Please delete "Chem Abstr. (23:335344f, 1993)".

Column 1,
Line 2, please delete "Artemesinin" and insert -- Artemisinin --.

Column 3, claim 1,
Line 22, please delete "extrtacting" and insert -- extracting --.
Line 22, between "extracting" and "ground", please insert -- the --.

Signed and Sealed this

Sixteenth Day of October, 2001

Attest:

NICHOLAS P. GODICI
*Attesting Officer*    *Acting Director of the United States Patent and Trademark Office*